United States Patent [19]

Spiller

[11] Patent Number: 5,423,750
[45] Date of Patent: Jun. 13, 1995

[54] TRANSPARENT COLOR-CODING OF INTRAVENOUS TUBING AND INTRAVENOUS FLUID RESERVOIR

[76] Inventor: Kenneth M. Spiller, 611 Roselawn Blvd., Lafayette, La. 70503

[21] Appl. No.: 168,470

[22] Filed: Dec. 16, 1993

Related U.S. Application Data

[63] Continuation-in-part of Ser. No. 792,685, Nov. 15, 1991, abandoned, which is a continuation-in-part of Ser. No. 571,710, Aug. 24, 1990, abandoned.

[51] Int. Cl.⁶ .............................................. A61M 5/14
[52] U.S. Cl. ..................................... 604/80; 604/173
[58] Field of Search .................................. 604/80–86, 604/56, 92, 173; 128/DIG. 26

[56] References Cited

U.S. PATENT DOCUMENTS

| | | | |
|---|---|---|---|
| 1,876,181 | 9/1932 | Tussing . | |
| 2,896,619 | 7/1959 | Bellamy, Jr. | 128/214 |
| 2,954,028 | 9/1960 | Smith | 128/214 |
| 3,698,383 | 10/1972 | Baucom | 128/2 G |
| 3,807,397 | 4/1974 | Noiles | 128/214 C |
| 4,072,146 | 2/1978 | Howes | 128/2.05 D |
| 4,150,673 | 4/1979 | Watt | 128/272 |
| 4,557,959 | 12/1985 | Kuehlein et al. | 428/36 |
| 4,619,640 | 10/1986 | Potolsky et al. . | |
| 4,654,026 | 3/1987 | Underwood | 604/80 |
| 4,795,429 | 1/1989 | Feldstein | 604/80 |
| 4,892,524 | 1/1990 | Smith | 604/246 |
| 5,224,932 | 7/1993 | Lappas | 604/80 |

FOREIGN PATENT DOCUMENTS

WO91/06255  5/1991  WIPO .

*Primary Examiner*—C. Fred Rosenbaum
*Assistant Examiner*—Perry E. Van Over
*Attorney, Agent, or Firm*—Pravel, Hewitt, Kimball & Krieger

[57] ABSTRACT

A system for the intravenous administration of single or multiple mendicants and/or nutrients to a patient through single or multiple intravenous tubings from single or multiple intravenous fluid sources where a portion of the intravenous tubing and a portion of the intravenous fluid source container are clearly marked with multiple indicia allowing for rapid visual identification and distinction between different tubes and containers, and where a section of the intravenous tubing at the patient's body and a section of the intravenous fluid container remains clear, colorless and transparent allowing for rapid and easy visual quality control and monitoring of the transfusion process. In a preferred embodiment, the multiple indicia comprise different colors, wherein each set of tubing and fluid reservoir is easily visually distinguished from the other, and also in the preferred embodiment the indicia is arranged in such a way so as to always provide a clear, colorless and transparent section of intravenous tubing immediately adjacent the injection site on the patient's body and a clear, colorless and transparent section of the container. Wherein said clear, colorless and transparent sections allowing easy visual quality control and monitoring of the transfusion.

14 Claims, 2 Drawing Sheets

TRANSPARENT COLOR-CODING OF INTRAVENOUS TUBING AND INTRAVENOUS FLUID RESERVOIR

CROSS REFERENCE TO RELATED APPLICATIONS

This application is a continuation-in-part of U.S. patent application Ser. No. 07/792,685, filed Nov. 15, 1991 now abandoned which was a continuation-in-part of U.S. patent application Ser. No. 07/571,710, filed Aug. 24, 1990, now abandoned.

BACKGROUND OF THE INVENTION

1. Field of the Invention

The present invention relates to the intravenous administration of liquid nutrients and/or medicants to a patient. More particularly, the present invention relates to the administration of single or multiple nutrients and/or medicants to a patient through the use of single or multiple intravenous fluid lines and single or multiple intravenous fluid reservoirs wherein a partial section of each reservoir and a partial section of each fluid line are color-coded, and a second portion of each is clear, the fluid lines being clear, colorless and transparent at the injection site.

2. General Background

The administration of liquid medicants and nutrients to patients via intravenous administration is a well established medical practice. Typically, the nutrient or medicant solution is delivered into the patient's bloodstream directly from an intravenous fluid line. Intravenous fluid lines generally consist of a flexible plastic tubing. In a typical intravenous fluid administration system, the intravenous fluid line connects directly with the source of the intravenous fluid. The fluid source is commonly an elevated intravenous fluid storage container that can be of flexible wall plastic construction, for example. In such a typical system, the flow of intravenous fluid to the patient is gravity driven. However, the intravenous fluid may also be pumped into the patient. Many such intravenous fluid pumps are patented.

It is not uncommon for a plurality of intravenous fluid lines, each connected to a different source of intravenous fluid, to simultaneously be used to deliver intravenous fluid therapy to a single patient. The simultaneous use of several different intravenous fluid lines (e.g., 9-10), each connected to a different source of intravenous fluid, is not uncommon in modern medical practice.

The simultaneous use of multiple intravenous fluid lines has led to some major problems in the current art of intravenous fluid administration, including problems with tubing course and rapid identification between multiple tubes. Further, the advances that have been made toward solving these problems have been severely limited by an inability to match utility with quality control.

One major disadvantage of current systems lies in the use of tubing to convey fluids from storage container to patient that is clear and transparent. Transparent clear tubing makes it difficult to monitor the course of the tube whether a single tube is in use or a plurality of tubes. This problem can lead to potentially dangerous disruptions in fluid flow resulting from kinks, tangles, or the like in the intravenous tubing. Such kinks create physical breaks in the continuity of the fluid communication between the patient's bloodstream and the source of the intravenous fluid.

Another significant disadvantage of current systems lies in the ability to easily distinguish between multiple intravenous fluid tubings. The clear and transparent nature of most intravenous fluid tubings makes it difficult to distinguish one line from the other in both routine care and in times of emergency treatment. This problem can become quite dangerous where confusion between different lines could lead to a mixing of incompatible medicants. For example, in the emergency treatment of a heart attack victim bearing several existing intravenous lines, the inability to quickly distinguish between a saline-infusing line and idocaine-infusing line into which to inject TPA could lead to severe consequences as the medicant TPA is incompatible with idocaine if injected into the same intravenous fluid line.

Some recent improvements in intravenous fluid administration technology have helped to ease some of the problems of current systems by easing the identification of multiple fluid lines. However, these improvements in ease of identification have come at the expense of ease of quality control.

Where the problem of rapid identification between multiple intravenous tubes and intravenous fluid reservoirs has been addressed, the result has been to place indicia throughout the entirety of either or both the intravenous tube and the intravenous fluid container. This use of indicia comes at the expense of ease of quality control, in that the indicia blocks or impairs the medical care provider's view of the course of the intravenous fluid administration.

Quality control is a necessary and vital component of the administration of intravenous fluids. Two critical means in which the health care provider monitors the quality of the intravenous fluid administration are to visually examine the fluid in the intravenous fluid container, and the fluid in the intravenous tubings as it enters the patient's body. By casually monitoring the course of the infusion, the medical care provider can be certain that the quality of the intravenous fluid is satisfactory and that the process of the administration is progressing satisfactorily. For example, visual monitoring of the intravenous tubing near the injection site can detect the backing of blood into the intravenous tubing, an indication of a troubled intravenous fluid administration. Also, for example, visual monitoring of the intravenous fluid reservoir can check for clarity of the fluid, the presence of contaminants, precipitation and so forth.

Hence, an unobstructed view of the fluid in both the intravenous tubing near the patient's body and in the intravenous fluid reservoir is critical to proper quality control in intravenous fluid administration. Any intravenous fluid administration that uses indicia which block an unobstructed view of the intravenous fluid at either or both the intravenous tubing near the patient's body and/or the intravenous fluid container suffers from a defect in quality control.

Only the instant invention both overcomes the problems associated with rapidly identifying and distinguishing between multiple intravenous tubings, and provides for a clear, unobstructed view of the intravenous fluid in both the intravenous tubing adjacent the injection site on the patient and in the intravenous fluid reservoir. Hence, only the instant invention both provides for rapid visual distinction between multiple IV tubes and provides ease of quality control.

Prior to the instant invention, other attempts to ease tube identification have come at the expense of quality control. For example, Lappas U.S. Pat. No. 5,224,932 discloses a system for intravenous administration of at least two different liquids to a patient where the tubing is of a translucent color throughout its entirety and where the fluid reservoir is of a translucent color throughout its entirety. Lappas clearly states that at least two distinct liquids are necessary. Further, Lappas does not disclose tubing with a clear section near the patient's body. The invention disclosed in Lappas is colored throughout its entirety. If the section of the tubing adjacent the patient's body is red, a nurse might not be able to see if blood had backed into that flowline.

Another important distinction between the instant invention and Lappas is that Lappas discloses the use of translucent–not transparent–tubing. The instant invention discloses the use of transparent–not translucent–tubing through its entirety. Both where the tubing is colored and where it is clear, the tubing in the instant invention remains transparent. Further, the injection port, base of the drip chamber and the adapter at the patient's body are transparent (clear and colorless)–not translucent–in the instant invention. This transparency is important in allowing for quality control monitoring throughout the course of the instant invention. For example, in the present invention, even in the colored portion of the tubing, a health care provider could visually monitor the fluid for both flow and the presence of particulate matter.

Emanuel PCT patent application WO 91/06255 discloses the use of colored tubing in the intravenous administration of a solution to a patient. A literal reading of the application would indicate that the color-coding is intended to encompass the entirety of the tubing. Further, the Emanuel patent application discloses colored or tinted drip chamber bases and adapters at the patient's body. The drip chamber and adapter at the patient's body in the present invention are clear, colorless and transparent. Thus, the Emanuel patent application does not disclose a clear section of tubing next to the patient's body nor does it address the use of a clear and transparent fluid reservoir that is only partially color coded, leaving a portion clear and colorless.

Kuehlein U.S. Pat. No. 4,557,959 discloses a multilayer working means for containing or transporting a physiological material wherein said working means contain additive agents which absorb radiation in the wave length range of visible light. However, the '959 patent is not addressed at color-coding IV tubing for purposes of identification. Further, a literal reading of the patent indicates that the coloring agent is to be distributed throughout the entirety of the tubing. Therefore, the Kuehlein patent does not disclose a clear section of tubing near the patient's body nor does it disclose anything about the color of an IV fluid reservoir.

Therefore, while the Lappas and Kuehlein patents, and the Emanuel patent application may disclose continuously colored tubing, they do not disclose colored tubing with clear sections, or clear IV fluid reservoirs for quality control.

Underwood U.S. Pat. No. 4,654,026 discusses the use of printed indicia along the tubing which is staggered.

Feldstein U.S. Pat. No. 4,795,429 uses colored tape or other indicia to stick on to transparent tubes.

Smith U.S. Pat. No. 4,892,524 discloses a metering device to control delivery volume. No mention is made of IV tube color or how to solve the problem of identifying the tube's course.

Howes U.S. Pat. No. 4,072,146 discloses a veni-puncture device and a venous catheter device. No application is made to IV tubing.

Watt U.S. Pat. No. 4,150,673 discloses only a colored-coded mating connector.

Baucom U.S. Pat. No. 3,698,383 discloses a device related to minimizing errors in blood handling procedures and blood transfusions. While the patent does address the use of removable indicia stuck to transfusion bags for purposes of identification, the patent does not address IV tubing, problems associated with identifying multiple IV tubing lines, and the use of color as an indica.

Bellamy U.S. Pat. No. 2,896,619 addresses the use of blood type identifying indicia on blood-containing IV bags. However, the patent does not address color-coding, IV tubing, or the problem of identifying multiple IV tubings.

Potolsky U.S. Pat. No. 4,619,640 does not address IV tubing. The patent discloses only the use of an opaquely colored connector.

Noiles U.S. Pat. No. 3,807,397 discloses only a flow meter for measuring the rate of flow of parenteral fluid traveling through a transparent tube. No mention is made of color-coding or to tubing identification.

Smith U.S. Pat. No. 2,954,028 discloses an apparatus for administering parenteral fluids to a patient. However, it does not address the use of color-coding with this apparatus.

Tussing U.S. Pat. No. 1,876,181 discloses a "display package of index guides" which essentially deals with the use of index cards. This invention has nothing to do with IV fluid administration.

Therefore, existing systems do not disclose an IV system wherein, while the tubing is color-coded to ease in identification of single or multiple IV lines, both the fluid reservoir and the section of the IV line near the patient's body are clear to allow for quality control in the transfusion process.

SUMMARY OF THE INVENTION

The object of the present invention is to provide an improved means of administering single or multiple intravenous fluids to a patient through single or multiple intravenous fluid lines. The nature of the improvement lies in combining an improved ease of visual identification and distinction between multiple intravenous fluid lines with an improved ease of visually monitoring the quality and course of the infusion.

Briefly, the invention comprises a system for the administration of single or multiple intravenous fluids through single or multiple intravenous fluid delivery administration sets wherein each said administration set is clearly marked by visual indicia so as to be easily distinguishable from each other and wherein each administration set also includes sufficient clear, colorless, and transparent sections to allow for easy and accurate quality control monitoring.

In accordance with the preferred embodiment, each set consists of a source of intravenous fluid and, an intravenous fluid line which maintains the patient's body in fluid communication with said fluid source. Each administration set is marked with indicia on both a portion of the intravenous tubing and the intravenous fluid reservoir; said indicia matching each other within each intravenous administration system; and each said administration system bearing an indicia that is visually distinct from all other administration systems used together in the multiple intravenous administration of a patient.

In accordance with the present invention, each section of indicia-bearing intravenous tubing also contains a clear, colorless and transparent section of intravenous tubing, and each indicia-bearing intravenous fluid storage container also contains a section that is clear, colorless and transparent. Said clear, colorless and transparent tubing section is located immediately adjacent to the injection site on the patient's body and runs to the first injection port. In accordance with the instant invention, said clear, colorless and transparent sections are sufficiently large and clear so as to allow a health care provider to easily and accurately visually inspect the course and quality of the intravenous fluid administration. In accordance with the preferred embodiment of the invention, in a transfusion with multiple intravenous fluids through multiple intravenous fluid tubings, each tubing and fluid reservoir indicia is of a different color, such that health care provider can rapidly, accurately, and easily distinguish between different tubings. In such an embodiment, a portion of the intravenous tubing and a portion of the intravenous fluid reservoir are marked with colored indicia, and in accordance with the present invention, a portion of the intravenous tubing running from the injection site on the patient's body to the injection port nearest the patient's body remains clear, colorless and transparent. Also, a portion of the intravenous fluid reservoir remains clear, colorless and transparent. In accordance with the preferred embodiment, the indicia on the indicia-bearing portion of the intravenous tubing is transparent. In accordance with the preferred embodiment, the indicia-bearing section of the intravenous fluid container is a colored patch or sticker, or more preferably, a partially colored region of transparent, translucent, or opaque color.

In accordance with the preferred embodiment, the present invention consists of either a single, or at least two different fluid administration sets, each set bearing a different visually distinguishable colored indicia. In accordance with the preferred embodiment, the health care provider can easily and rapidly follow the course of each tube as well as identify and distinguish between different administration sets by examining either or both the intravenous tubing or the intravenous fluid reservoir. Further, in accordance with the present invention, the health care provider can easily and accurately examine the quality and course of the intravenous fluid administration by examining the fluid through the clear, colorless and transparent sections in both the intravenous tubing adjacent to the patient's body and the intravenous fluid reservoir.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
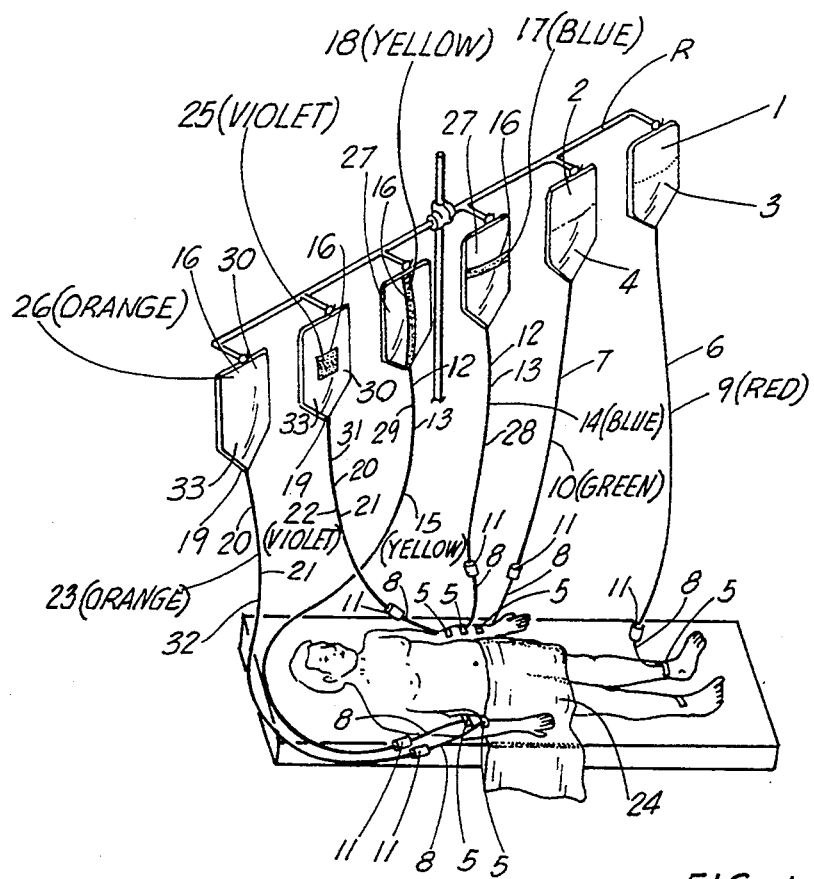
FIG. 1 represents a perspective view of a system for intravenous administration of multiple fluids through multiple intravenous fluid lines to a patient in accordance with the present invention.

FIG. 1 illustrates a system for intravenous administration of multiple intravenous fluids through multiple intravenous fluid lines to a patient in accordance with the present invention. In FIG. 1, patient 24 is in fluid communication with multiple intravenous fluid administration sets, which are color-coded for easy identification and which contain clear, colorless and transparent sections for easy quality control.

In FIG. 1, first intravenous fluid storage container 1 is suspended from rack R at a height above patient 24 sufficient for gravity feeding of first volume of intravenous fluid 3 into the patient 24. First intravenous fluid storage container 1 is connected to first length of intravenous tubing 6. First length of intravenous tubing 6 is attached to injection port 11. Injection port 11 is further attached to clear, colorless and transparent tubing portion 8 which connects at its opposite end to injection site 5 on patient 24 (see FIG. 2). These parts 1, 6, 11, 8 and 5 are connected in such a manner as to allow fluid communication between patient 24 and first intravenous fluid 3.

First color-coded indicia 9 is located on both first intravenous fluid storage container 1 and on first length of intravenous tubing 7. In the preferred embodiment represented in FIG. 1, the first color-coding indicia is of the color red. The section of tubing 6 between injection port 11 and container 1 is entirely color coded as red tubing. The section of tubing 8 between injection port 11 and injection port 5 is clear and colorless. This pattern of a colored tubing section from the container to an injection port, and a clear colorless section of tubing at the injection site holds true for all six of the fluid container and IV tubing systems shown in FIG. 1. In this manner, the physician or nurse can quickly identify a particular tubing as conveying a particular fluid, yet each tubing is clear and colorless at the injection site for inspection of the fluid being conveyed, its color, the presence of bubbles, etc.

Also shown in FIG. 1 are second intravenous fluid storage container 2, filled with second volume of intravenous fluid 4, which is attached to second length of intravenous tubing 7. Second length of intravenous tubing 7 is further attached to injection port 11, which is attached to clear, colorless transparent tubing portion 8 which is attached at its opposite end to injection site 5 on the patient 24. Similar to the above-described parts 1, 6, 11, 8 and 5, the parts 2, 7, 11, 8 and 5 are connected in such a manner as to allow fluid communication between the second volume of intravenous fluid 4 and patient 24. Also in a manner similar to above-mentioned parts 1 and 6, parts 2 and 7 are marked with second color-coding indicia 10. In the preferred embodiment of FIG. 1, the second color-coding indicia 10 is of the color green.

FIG. 1 also illustrates two intravenous fluid administration sets wherein indicia-bearing tubing section 12 is marked with tubing indicia 13, and intravenous fluid storage container 27 is marked with container indicia 16. In FIG. 1, the intravenous fluid storage container 27 is connected to the indicia-bearing tubing section 12 which is connected at its opposite end to injection port 11. Injection port 11 is further connected to clear, colorless and transparent tubing portion 8 which connects at its opposite end to injection site 5 on the patient 24. Parts 27, 12, 11, 8 and 5 are arranged so that patient 24 is in fluid communication with the source of intravenous fluid in fluid storage container 27. In the preferred embodiment of FIG. 1, tubing indicia 13 is of both a first tubing indicia 14 which is of the color blue on the first administration set 28, and the second fluid administration set 29, a second tubing indicia 15 is of the color yellow. Also, in the preferred embodiment of FIG. 1, container indicia 16 is of both a first container indicia 17 which is of the color blue on the first administration set 28, and on the second administration set 29, a second container indicia 18 is of the color yellow.

In the preferred embodiment of FIG. 1, first administration set 28 is marked with blue indicia on both the container and the intravenous tubing, and the container administration set 29 is marked with yellow on both the container and the tubing.

The preferred embodiment illustrated in FIG. 1 shows fluid storage container 30 connected via fluid container outlet 19 to colored intravenous tubing 20. Colored intravenous tubing 20 is further connected to injection port 11 which connects the colored intravenous tubing 20 to clear, colorless and transparent tubing portion 8 which is attached opposite injection port 11 to injection site 5 on the patient 24. Parts 30, 19, 20, 11, 8 and 5 are connected in such a manner as to allow fluid communication between the source of intravenous fluid in the fluid container 30 with the patient 24.

Fluid storage container 30 is marked with colored container indicia 33, and the colored indicia tubing 20 is marked with intravenous tubing indicia 21. In the preferred embodiment of FIG. 1, first set 31 is marked with both first colored intravenous tubing indicia 22 and first container indicia 25; both indicia 22 and 25 being of the color violet. In the preferred embodiment of FIG. 1, second set 32 is marked with both second colored intravenous tubing indicia 23 and second color container indicia 26; both indicia 23 and 26 being of the color orange.

Figure 2:
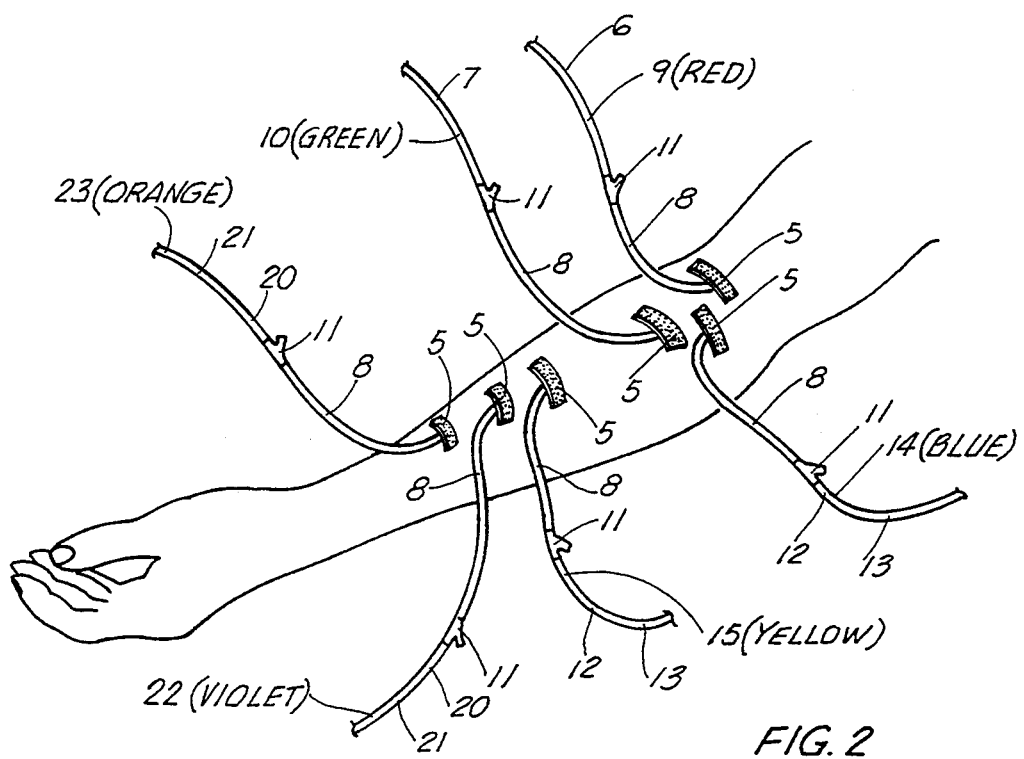
FIG. 2 is an illustration of multiple injection sites on a patient's arm, multiple first clear, colorless and transparent sections of tubings, multiple first injection ports, and multiple portions of the indicia-bearing intravenous tubing.

FIG. 2 illustrates a close-up view of clear, colorless and transparent portion 8, also illustrated in FIG. 2 are injection sites 5 on patient 24, injection ports 11, and associated indicia-bearing intravenous tubing. Of particular note in FIG. 2 is the location of clear, colorless and transparent tubing section 8 relative to injection site 5 on patient 24 and to injection port 11.

In the preferred embodiment as depicted in FIG. 2, approximately the first several inches (for example, five - 10 inches) of the intravenous tubing remains clear, colorless and transparent running from the patient's body to the first injection port 11. Both the location of this section 8 and its clear, colorless and transparent quality are important for monitoring the quality of the infusion. For example, a common indicator of a faulty transfusion is the backing up of blood into the beginning of the intravenous fluid line. In the preferred embodiment illustrated in FIG. 2, through part 8 the health care provider can easily and quickly visually monitor the flow of intravenous into the patient without the colored tubing indicia blocking the view.

Figure 3:
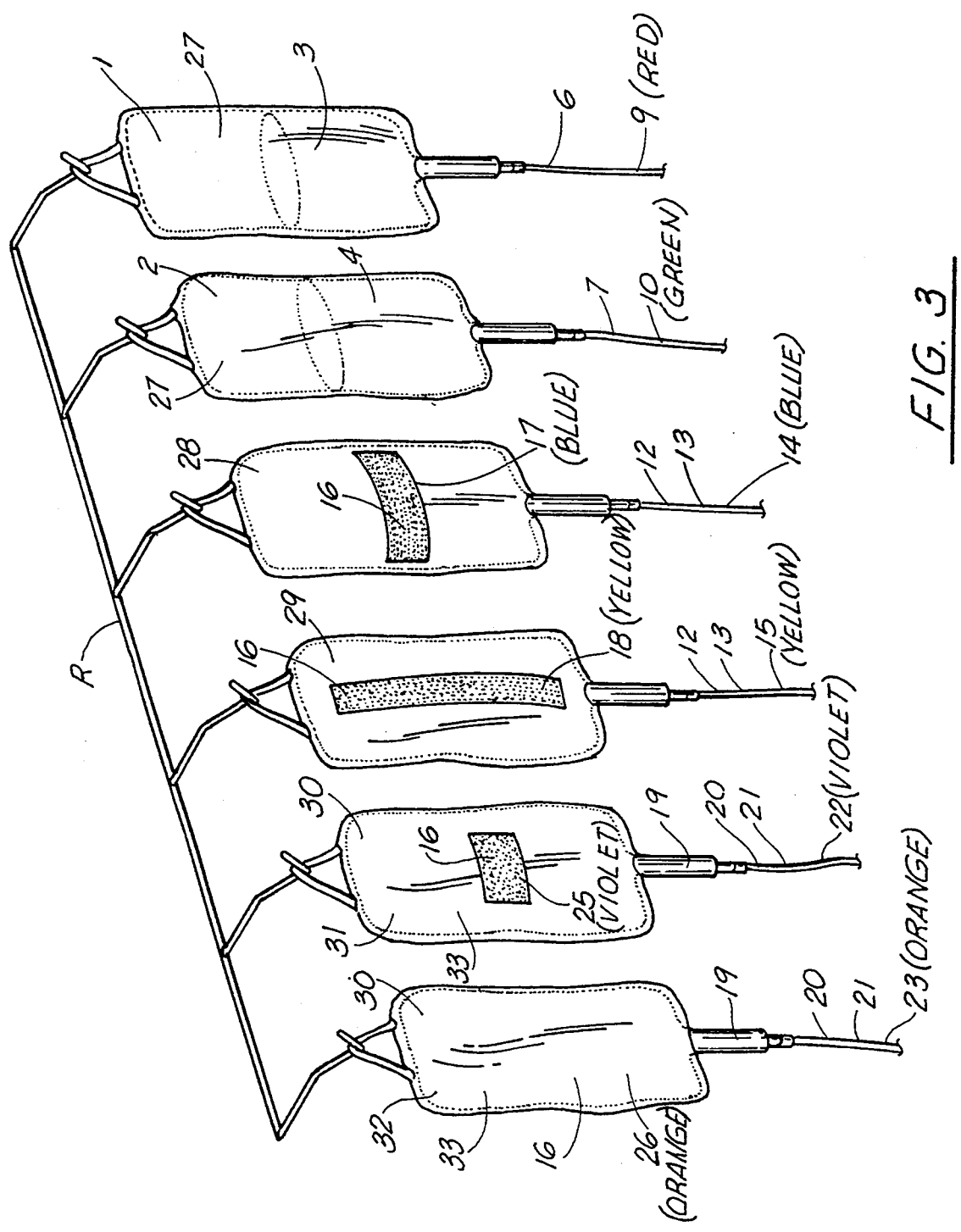
FIG. 3 is an illustration of multiple intravenous fluid containers, intravenous container outlets, intravenous fluid container indicia, and multiple portions of indicia-bearing intravenous tubing.

FIG. 3 is a close-up view of the intravenous fluid storage containers and attached intravenous tubes described more fully in FIG. 1. Of particular note in the Figure is container indicia 16. In the preferred embodiment as depicted in FIG. 2, container indicia 16 is either a horizontal strip color as in first administration set 28, a vertical stripe of color as in second administration set 29, a patch of color as in first set 31, or diffuse color as in second administration set 32. Note that container indicia 16 as depicted in FIG. 2, parts 28, 29 and 30 could consist of either a permanently affixed or embedded container indicia, or a removable adhesive indicia.

The following table lists the parts numbers and parts descriptions as used herein and in the drawings attached hereto.

| Part Number | PARTS LIST<br>Description |
| --- | --- |
| 1 | first intravenous fluid storage container |
| 2 | second intravenous fluid storage container |
| 3 | first volume of intravenous fluid |
| 4 | second volume of intravenous fluid |
| 5 | injection site |
| 6 | first length of intravenous tubing |
| 7 | second length of intravenous tubing |
| 8 | clear, colorless and transparent tubing portion |
| 9 | first color-coding indicia (red) |
| 10 | second color-coding indicia (green) |
| 11 | injection port |
| 12 | indicia-bearing tubing section |
| 13 | tubing indicia |
| 14 | first tubing indicia (blue) |
| 15 | second tubing indicia (yellow) |
| 16 | container indicia |
| 17 | first container indicia (blue) |
| 18 | second container indicia (yellow) |
| 19 | fluid container outlet/ drip chamber |
| 20 | colored intravenous tubing |
| 21 | colored intravenous tubing indicia |
| 22 | first colored intravenous tubing indicia (violet) |
| 23 | second colored intravenous tubing indicia (orange) |
| 24 | patient |
| 25 | first colored container indicia (violet) |
| 26 | second colored container indicia (orange) |
| 27 | intravenous fluid storage container |
| 28 | first administration set |
| 29 | second administration set |
| 30 | fluid storage container |
| 31 | first set |
| 32 | second set |
| 33 | colored container indicia |
| R | rack |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as the invention is:

1. A system for intravenous administration of at least two different fluids through at least two different intravenous tubes to a patient, said system comprising:
   a) first and second intravenous fluid storage containers for storing first and second volumes of intravenous fluids for transfusion into a patient's bloodstream at two spaced apart, first and second injection sites on the patient's body;
   b) first and second lengths of intravenous tubing, connected between said first and second intravenous fluid storage containers and said first and second injection sites on said patient's body;
   c) said first length of intravenous tubing being connected between said first intravenous fluid storage container and said first injection site, said first length of intravenous tubing thereby allowing fluid communication between said first volume of intravenous fluid and said patient's blood stream via said first injection site;
   d) said second length of intravenous tubing being connected between said second intravenous fluid storage container and said second injection site, said second length of intravenous tubing thereby allowing fluid communication between said second volume of intravenous fluid and said patient's blood stream via said second injection site:
   e) said first and second lengths of intravenous tubing each being subdivided into two sections each, a proximal section, and a distal section;
   f) each said proximal section located proximal to the patient, in connection with each said injection site on said patient's body and running toward each said intravenous fluid storage container;
   g) each said distal section located distal to the patient, in connection with each said intravenous fluid storage container and running toward said patient's body;
   h) each said proximal section being shorter than each said distal section, each said proximal section beginning at each said injection site on said patient's body and running a short distance from each said injection site, with each said distal section running the remaining distance to each said intravenous fluid storage container;
   i) each said proximal section being clear, colorless and transparent;
   j) each said distal section being colored continuously and completely throughout its entirety;
   k) said color of each said distal section being transparent in nature, such that each said distal section is transparent throughout its entirety as well as being colored continuously and completely throughout its entirety;
   l) color of said distal tubing section of said first length of intravenous tubing being of a first tubing color; and
   m) color of said distal tubing section of said second length of intravenous tubing being of a second tubing color.

2. The system for intravenous administration of at least two different fluids through at least two different intravenous fluid lines to a patient as defined in claim 1, wherein:
   a) said first intravenous fluid storage container is of a first container color;
   b) said first container color being the same color as said first tubing color;
   c) said second intravenous fluid storage container is of a second container color; and
   d) said second container color being of the same color as said second tubing color.

3. The system for intravenous administration of at least two different fluids through at least two different intravenous fluid lines to a patient as defined in claim 1, wherein each said proximal section is about 5–10 inches in length.

4. The system for intravenous administration of at least two different fluids through at least two different intravenous fluid lines to a patient as defined in claim 1, wherein said color of each said distal section is impregnated into the tube, said color being continuous and transparent.

5. A system for intravenous administration of fluids through intravenous tubes to a patient, said system comprising:
   a) an intravenous fluid storage container for storing a volume of intravenous fluid for transfusion into a patient's bloodstream at an injection site on the patient's body;
   b) a length of intravenous tubing, connected between said intravenous fluid storage container and said injection site on said patient'body;
   c) said length of intravenous tubing allowing fluid communication between said volume of intravenous fluid in said intravenous fluid storage container and said patient's blood stream via said injection site on said patient's body;
   d) said length of intravenous tubing being subdivided into two sections, a proximal section, and a distal section;
   e) said proximal section located proximal to the patient, in connection with said injection site on said patient's body and running toward said intravenous fluid storage container;
   f) said distal section located distal to the patient, in connection with said intravenous fluid storage container and running toward said patient's body;
   g) said proximal section being shorter than said distal section, said proximal section beginning at said injection site on said patient's body and running a short distance from said injection site, with said distal section running the remaining distance to said intravenous fluid storage container;
   h) said proximal section being clear, colorless and transparent;
   i) said distal section being colored continuously and completely throughout its entirety; and
   j) said coloring of said distal section being transparent in nature, such that said distal section is transparent throughout its entirety as well as being colored continuously and completely throughout its entirety.

6. The system for the intravenous administration of fluids through intravenous tubes to a patient as defined in claim 5, wherein said intravenous fluid storage container is colored, said color of said intravenous fluid storage container being of the same color as said color of said distal section of intravenous tubing.

7. The system for the intravenous administration of fluids through intravenous tubes to a patient as defined in claim 5, wherein said proximal section is about 5–10 inches in length.

8. The system for the intravenous administration of fluids through intravenous tubes to a patient as defined in claim 5, wherein said color of said distal section tubing is impregnated into the tube, said color being continuous and transparent.

9. A system for intravenous administration of at least two different fluids through at least two different intravenous tubes to a patient, said system comprising:
   a) first and second intravenous fluid storage containers for storing first and second volumes of intravenous fluids for transfusion into a patient's bloodstream at two spaced apart, first and second injection sites on the patient's body;
   b) first and second lengths of intravenous tubing, connected between said first and second intravenous fluid storage containers and said first and second injection sites on said patient's body;
   c) said first length of intravenous tubing being connected between said first intravenous fluid storage container and said first injection site, said first length of intravenous tubing thereby allowing fluid communication between said first volume of intravenous fluid and said patient's blood stream via said first injection site;
   d) said second length of intravenous tubing being connected between said second intravenous fluid storage container and said second injection site, said second length of intravenous tubing thereby allowing fluid communication between said second volume of intravenous fluid and said patient's blood stream via said second injection site;
   e) said first and second lengths of intravenous tubing each subdivided into two sections each, a proximal section, and a distal section;
   f) each said proximal and each said distal sections being divided by an injection port;
   g) each said injection port allowing fluid communication between each said proximal and each said distal sections of tubing;
   h) each said proximal section located proximal to the patient, in connection with each said injection site on said patient's body and running toward each said injection port;
   i) each said distal section located distal to the patient, in connection with each said intravenous fluid storage container and running toward each said injection port;
   j) each said proximal section being shorter than each said distal section, each said proximal section beginning at each said injection site on said patient's body and running a short distance from each said injection site to each said injection port, with each said distal section running the remaining distance from each said injection port to each said intravenous fluid storage container;
   k) each said proximal section being clear, colorless and transparent;
   l) each said distal section being colored continuously and completely throughout its entirety;
   m) said coloring of each said distal section being transparent in nature, such that each said distal section of tubing is transparent throughout its entirety as well as being colored continuously and completely throughout its entirety;
   n) said color of each said distal section of said intravenous tubing being impregnated into the tube, said color being continuous and transparent;
   o) the color of said distal tubing section of said first length of intravenous tubing being of a first tubing color; and
   p) the color of said distal tubing section of said section length of intravenous tubing being of a second tubing color.

10. The system for the intravenous administration of at least two different fluids through at least two different intravenous tubes to a patient as defined in claim 9, wherein each said proximal section is about 5-10 inches in length.

11. The system for the intravenous administration of at least two different fluids through at least two different intravenous tubes to a patient as defined in claim 9, wherein said injection ports are clear, colorless and transparent.

12. A system for intravenous administration of fluids through intravenous tubes to a patient, said system comprising:
   a) an intravenous fluid storage container for storing a volume of intravenous fluid for transfusion into a patient's bloodstream at an injection site on the patient's body;
   b) a length of intravenous tubing, connected between said intravenous fluid storage container and said injection site on said patient's body;
   c) said length of intravenous tubing allowing fluid communication between said volume of intravenous fluid and said patient's blood stream via said injection site on said patient's body;
   d) said length of intravenous tubing being subdivided into two sections, a proximal section, and a distal section;
   e) said proximal and said distal sections being divided by an injection port;
   f) said injection port allowing fluid communication between said proximal and said distal sections of tubing;
   g) said proximal section located proximal to the patient, in connection with said injection site on said patient's body and running toward said injection port;
   h) said distal section located distal to the patient, in connection with said intravenous fluid storage container and running toward said injection port;
   i) said proximal section being shorter than said distal section, said proximal section beginning at said injection site on said patient's body and running a short distance from said injection site to said injection port, with said distal section running the remaining distance from said injection port to said intravenous fluid storage container;
   j) said proximal section being clear, colorless and transparent;
   k) said distal section being colored continuously and completely throughout its entirety;
   l) said color of said distal section being transparent in nature, such that said distal section is transparent throughout its entirety as well as being colored continuously and completely throughout its entirety; and
   m) said color of said distal section being impregnated into the tube, said color being continuous and transparent.

13. The system for intravenous administration of fluids through intravenous tubes to a patient as defined in claim 12, wherein said proximal section of intravenous tubing is about 5-10 inches in length.

14. The system for intravenous administration of fluids through intravenous tubes to a patient as defined in claim 12, wherein said injection port is clear, colorless and transparent.

* * * * *